United States Patent
Schulze et al.

(10) Patent No.: US 8,474,329 B2
(45) Date of Patent: Jul. 2, 2013

(54) PIPE-SHAPED SENSOR DEVICE

(75) Inventors: Werner Schulze, Göttingen (DE); Michael Wald, Hildesheim (DE)

(73) Assignee: Otto Bock Healthcare Products GmbH, Vienna (AT)

( * ) Notice: Subject to any disclaimer, the term of this patent is extended or adjusted under 35 U.S.C. 154(b) by 179 days.

(21) Appl. No.: 12/918,561

(22) PCT Filed: Feb. 5, 2009

(86) PCT No.: PCT/EP2009/000778
§ 371 (c)(1), (2), (4) Date: Nov. 17, 2010

(87) PCT Pub. No.: WO2009/103423
PCT Pub. Date: Aug. 27, 2009

(65) Prior Publication Data
US 2011/0060249 A1  Mar. 10, 2011

(30) Foreign Application Priority Data
Feb. 21, 2008  (DE) .......................... 10 2008 010 281

(51) Int. Cl.
*G01L 1/00* (2006.01)
(52) U.S. Cl.
USPC .................................. 73/862.041
(58) Field of Classification Search
USPC .................... 73/862.041, 862.08
See application file for complete search history.

(56) References Cited

U.S. PATENT DOCUMENTS

| | | | |
|---|---|---|---|
| 4,932,253 A | 6/1990 | McCoy | |
| 6,918,308 B2 * | 7/2005 | Biedermann et al. | 73/862.629 |
| 7,455,696 B2 * | 11/2008 | Bisbee et al. | 623/45 |
| 7,500,407 B2 | 3/2009 | Boiten | |
| 8,181,539 B2 * | 5/2012 | Delatorre | 73/862.338 |
| 2003/0094081 A1 | 5/2003 | Becker et al. | |

(Continued)

FOREIGN PATENT DOCUMENTS

| | | |
|---|---|---|
| DE | 2856607 B1 | 7/1980 |
| DE | 8234075 U1 | 4/1984 |

(Continued)

OTHER PUBLICATIONS

PCT International Search Report for PCT International Application No. PCT/EP2009/000778, mailed Jul. 8, 2009.

*Primary Examiner* — Freddie Kirkland, III
(74) *Attorney, Agent, or Firm* — Holland & Hart LLP

(57) ABSTRACT

The invention relates to a sensor device (1) for measuring an axial force in the longitudinal pipe direction of a pipe (4) and/or at least one torque, having a measuring element (2) comprising an adapter connection (3) connected to the pipe by means of a flanged socket part, by means of which the pipe can be fixedly coupled to an adjustment adapter (5), wherein the axial force and the torque can be fed into the adjustment adapter and can be measured by means of strain gauges (11, 12) disposed in a sensor area (9) between the adapter connection and an end of the flanged socket part (6) opposite the adapter connection at strain gauge locations, wherein the flanged socket part having the sensor area is designed in a pipe shape, wherein the sensor area extends from the adapter connection to the end of the flanged socket part and has a smaller outer diameter than the end of the flanged socket part, wherein the end of the pipe facing the adapter connection and extending past the end of the flanged socket part toward the adapter connection is force decoupled from the sensor area and from the adapter connection, and wherein at least three strain gauge measuring locations are disposed on the circumference of the sensor area.

24 Claims, 3 Drawing Sheets

U.S. PATENT DOCUMENTS

2007/0255424 A1    11/2007    Leydet et al.
2008/0276725 A1    11/2008    Pusch

FOREIGN PATENT DOCUMENTS

| | | | |
|---|---|---|---|
| DE | 3405168 A1 | 8/1985 |
| DE | 3528364 A1 | 2/1987 |
| DE | 102005051495 A1 | 5/2007 |
| EP | 1143230 A2 | 10/2001 |
| EP | 1559384 A1 | 8/2005 |
| EP | 1143230 B1 | 8/2009 |

\* cited by examiner

PIPE-SHAPED SENSOR DEVICE

FIELD OF THE INVENTION

The invention relates to a sensor device for measuring an axial force in the longitudinal pipe direction of a pipe and/or at least one torque with a measuring element which has an adaptor connection, which is connected to the pipe by means of a pipe extension piece and which can be used to firmly couple the pipe to an alignment adaptor, wherein the axial force and the torque can be introduced into the alignment adaptor by means of the measuring element and can be measured by means of strain gauges which are arranged at DMS measuring points in a sensor region between the adaptor connection and an end of the pipe extension piece which is remote from the adaptor connection.

BACKGROUND

Such sensor devices can be used for pipe constructions, for example, generally or specifically for handling devices or industrial robots or for prostheses.

By way of example, a sensor device for measuring a torque transversely with respect to the longitudinal pipe direction of the pipe is known from the company Otto Bock Healthcare GmbH in Duderstadt. In this case, the pipe is used for the connection between a controllable artificial knee joint and a prosthetic foot. The pipe can be connected to the knee joint by means of a clamp arranged on the knee joint. In this case, the prosthetic foot has what is known as an alignment adaptor to which the pipe can be firmly coupled by means of an adaptor connection, connected thereto, using alignment screws and can be aligned within certain limits. The adaptor connection has a pipe extension piece which is integrally formed on the adaptor connection, wherein the pipe has its end facing the adaptor connection pushed over the pipe extension piece and cemented thereto. In this case, the pipe extension piece and the adaptor connection form a measuring element which can be used to introduce the axial force and the torque into the alignment adaptor and to measure them using strain gauges arranged on the pipe extension piece.

The known pipe extension piece comprises, in principle, a cylindrical extension which is integrally formed on the adaptor connection and which has a perforation transversely with respect to its longitudinal axis and has its front side which faces away from the adaptor connection connected to the base area of a pot-shaped end of the extension piece via two integrally formed web-shaped bars which are opposite one another. The two webs form a sensor region with a respective measuring point having four strain gauges arranged in a bridge circuit. Both the cylindrical extension and the pot-shaped extension have their generated surface cemented to the pipe wall of the pipe.

A drawback in this context is that firstly the measuring element with its pipe extension piece is of relatively complicated and hence costly design and that secondly the demarcation of the axial force from the disturbance loads and the torques to be measured is problematical.

In addition, EP 1 559 384 B1 discloses a sensor device or a torque sensor for measuring a torque which is designed as a sensor structure forming a virtual axis of rotation outside of the sensor and which is arranged directly below the knee joint. In this case, the torque sensor or the measuring element has a multijoint structure with elastically deformable joints.

A drawback in this case is that the measuring element is of relatively complex design and takes up installation space which may already be occupied by fundamental functional elements.

In addition, DE 10 2005 051 495 A1 discloses a sensor arrangement for measuring forces and torques in which the measuring element is in the form of part of an alignment adaptor.

A drawback in this case is that the alignment adaptor is of relative voluminous and complex design.

SUMMARY

It is therefore an object of the present invention to provide a measuring sensor which is simple and inexpensive to produce and which allows reproducible, reliable and fast ascertainment of both axial forces and torques.

This object is achieved in connection with the preamble of claim 1 in that the pipe extension piece with the sensor region is of tubular design, in that the sensor region extends from adaptor connection to the end of the pipe extension piece and has a smaller external diameter than the end of the pipe extension piece, in that the pipe has its end which faces the adaptor connection and which overtops the end of the pipe extension piece toward the adaptor connection decoupled in terms of force from the sensor region and from the adaptor connection, and in that at least three DMS measuring points are arranged on the perimeter of the sensor region.

The tubular design of the pipe extension piece and of the sensor region makes it possible to dispense with weight-reducing perforations transversely with respect to the longitudinal direction. Since the sensor region extends over the entire length of the pipe extension piece between the adaptor connection and that end of the pipe extension piece which is remote from the adaptor connection and has a smaller external diameter than the end of the pipe extension piece, the sensor region is spaced apart from the inner sheath of the pipe that surrounds it and allows a clear distinction between the axial force in the longitudinal pipe direction and torques acting transversely with respect to the longitudinal pipe direction or around the longitudinal pipe direction. Only the end of the pipe extension piece is firmly connected to the pipe, so that the end of the pipe which overtops the end of the pipe extension piece toward the adaptor connection in the sensor region is decoupled in terms of force from the sensor region and from the adaptor connection. This results in a relatively lightweight, simple and inexpensive design with clear force transmission mechanisms and corresponding simpler reproducible measurability.

The object is also achieved in connection with the preamble of claim 2 in that the pipe extension piece with the sensor region is of tubular design, in that the sensor region extends from the adaptor connection to the end of the pipe extension piece and has a smaller external diameter than the end of the pipe extension piece, in that the pipe extension piece is integrally formed on that end of the pipe which faces the adaptor connection, in that at least 3 DMS points are arranged on the perimeter of the sensor region, and in that the sensor region is covered by a cover which is mounted on the pipe and which is decoupled in terms of force from the sensor region and from the adaptor connection.

The one-piece design of the pipe extension piece and the pipe does not require a separate adhesive bond. The cover required for protecting the DMS measuring points or the sensor region is provided in the case of the one-piece design by a cover which is additionally mounted on the pipe but which can be fitted with relatively few problems on account of the decoupling in terms of force on the sensor region and the adaptor connection.

Depending on the application, the present sensor apparatus can be used to measure the axial force in the longitudinal pipe direction and/or torques transversely with respect to the longitudinal pipe direction or else around the longitudinal pipe direction. It goes without saying that suitable sensors can also be used to measure forces at right angles to the longitudinal pipe direction.

In line with one preferred embodiment of the invention, the pipe or the cover is sealed from the adaptor connection by an elastic seal. An elastic seal prevents the penetration of water without overriding the decoupling in terms of force from the adaptor connection and from the sensor region.

The alignment adaptor and the adaptor connection are fixed to one another by means of at least three alignment screws, wherein the number of measuring points in the sensor region corresponds at least to the number of alignment screws.

In line with a further preferred embodiment of the invention, the alignment adaptor is in the form of an inverted pyramid frustum and has four planar alignment faces which run obliquely with respect to the longitudinal axis which interact with four alignment screws arranged in the adaptor connection, wherein the pyramid frustum merges into a sphere-section-shaped base which corresponds with a corresponding annular contact face of the adaptor connection. In this case, eight DMS measuring points are arranged on the perimeter of the sensor region. The eight DMS measuring points are arranged in a radial plane with a respective 22.5 degrees offset from four alignment screws having a 90 degrees offset.

A number of DMS measuring points which corresponds to twice the number of alignment screws has proven itself especially. In principle, torques occurring at least transversely with respect to the longitudinal pipe direction and an axial force in the longitudinal pipe direction can be ascertained from the eight measuring points. Since the torque occurring and the axial force usually correspond to signal sizes of varying order of magnitude, however, it has proven worthwhile to arrange additional DMS measuring points on the perimeter of the sensor region for the purpose of separate ascertainment of the axial force. In this case, four additional DMS measuring points may be arranged in a radial plane in association with the four alignment screws, for example.

According to a further preferred embodiment of the invention, each measuring point has two strain gauges which are arranged next to one another in the longitudinal pipe direction with a measuring grid orientation having a 90 degrees offset from one another.

In line with a further preferred embodiment of the invention, the adaptor connection is produced from titanium in one piece with the pipe extension piece.

This has the advantage that the adaptor connection has relatively high strength for low weight and a relatively thin pipe wall in the sensor region.

By way of example, the sensor device can be used in an artificial leg or a robot arm of a handling apparatus.

Further details of the invention can be found in the following detailed description and the appended drawings, which illustrate preferred embodiments of the invention by way of example.

DESCRIPTION OF THE EXEMPLARY EMBODIMENTS

Figure 1:
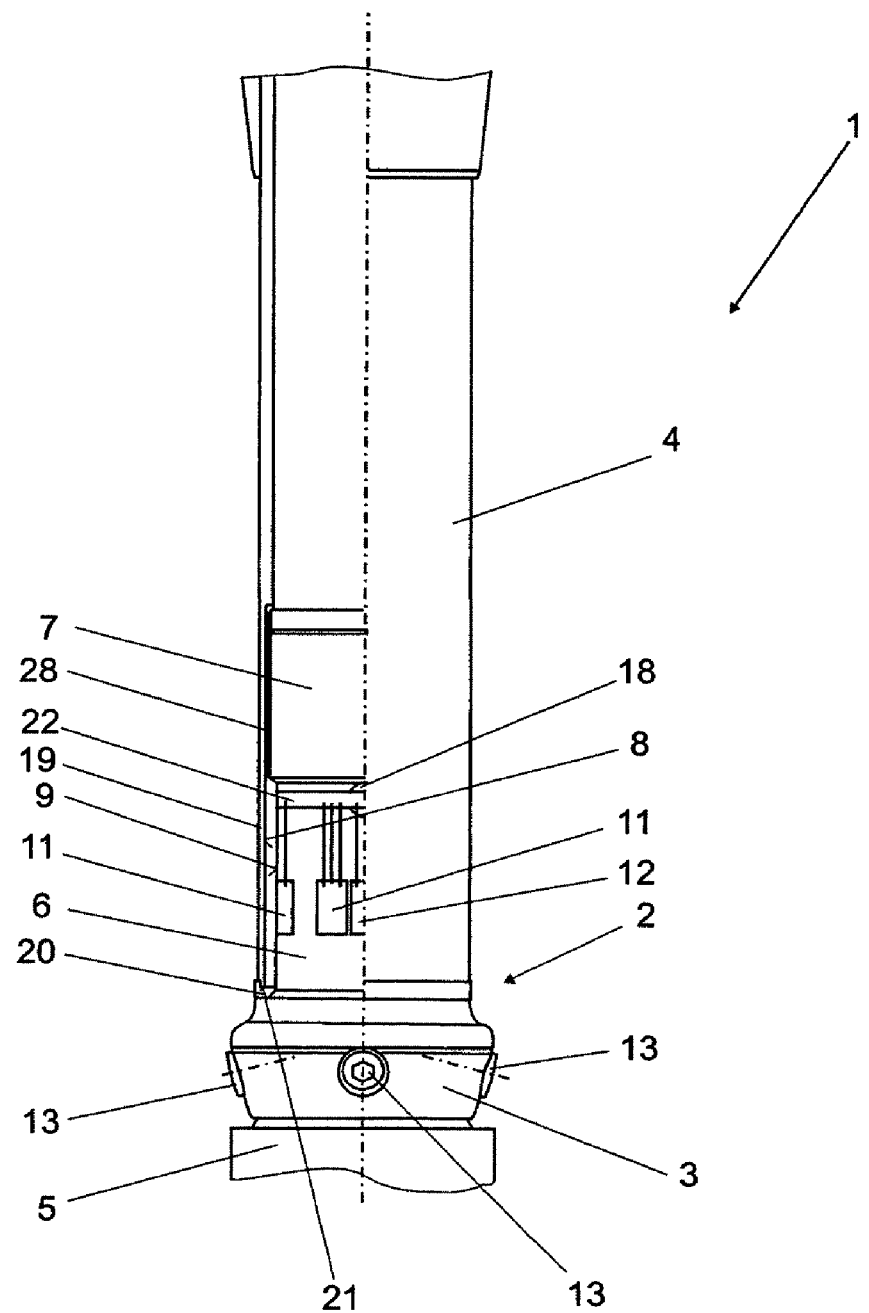
FIG. 1 shows a side view of a sensor device having a measuring element arranged in a pipe, wherein the pipe is shown with an elastic seal in half-section.
Figure 2:
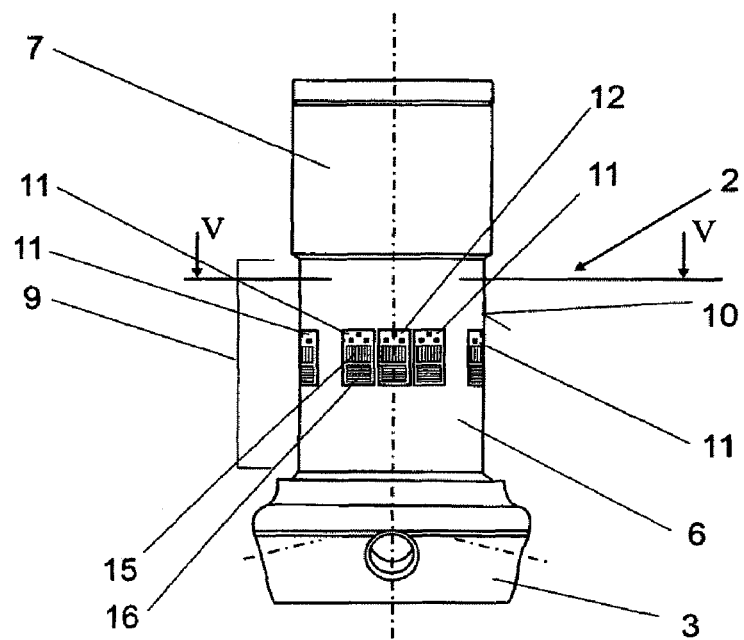
FIG. 2 shows a front view of the measuring element from FIG. 1.
Figure 3:
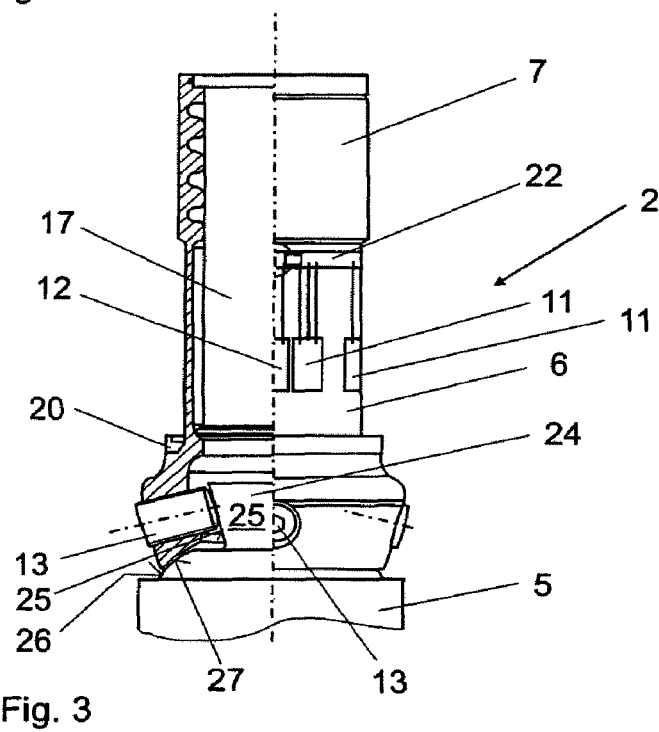
FIG. 3 shows a side view in half-section of the measuring element from FIG. 1 with a coupled alignment adaptor.
Figure 4:
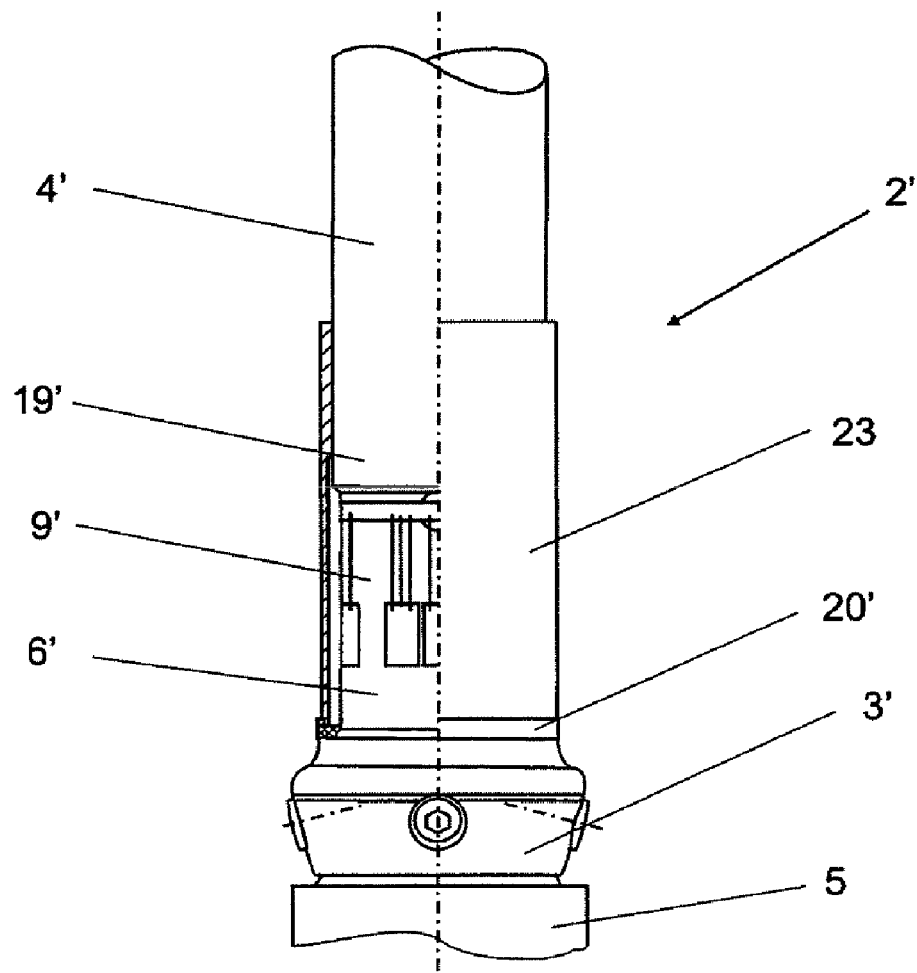
FIG. 4 shows a side view of a measuring element, integrally formed on a pipe, with a coupled alignment adaptor and a cover of the sensor region in half-section.
Figure 5:
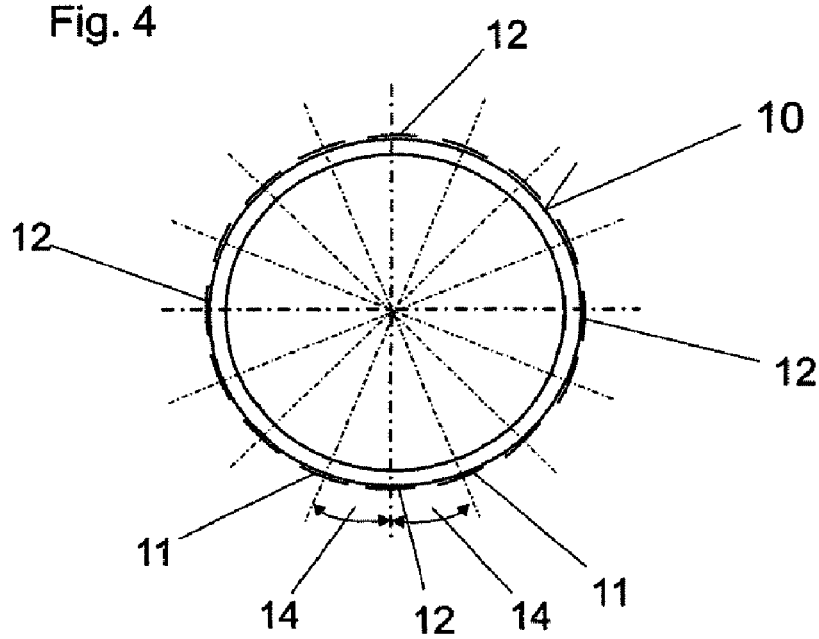
FIG. 5 shows a plan view of the sensor region from FIG. 2 in the section along the line V-V.

A sensor device 1 essentially comprises a measuring element 2 with an adaptor connection 3 which can be used to couple a pipe 4 to an alignment adaptor 5.

The measuring element 2 comprises a pipe extension piece 6 which has the adaptor connection 3 at its first end. The pipe extension piece 6 can have its free end 7 which is remote from the adaptor connection 3 inserted into the pipe 4 and can be cemented to the inner pipe wall 8 of the pipe 4 using an adhesive 28. The free end 7 and the adaptor connection 3 have a sensor region 9 between them which has a smaller external diameter 10 than the free end 7. In the exemplary embodiment, eight DMS measuring points 11 for determining torque and four DMS measuring points 12 for determining axial force are arranged on the perimeter of the sensor region 9. The eight DMS measuring points 11 for determining torque are arranged in a radial plane with an offset of a respective angle 14 of 22.5° from four alignment screws 13 having a 90° offset in the adaptor connection 3. The DMS measuring points 12 for determining axial force are associated with the alignment screws 13 in the radial plane and are therefore situated between two DMS measuring points 11 for determining torque. Each of the measuring points 11, 12 has two respective strain gauges 15, 16 which are arranged next to one another in the pipe longitudinal direction with a measuring grid orientation having a 90° offset from one another. The strain gauges 15, 16 are adhesively bonded on the perimeter of the sensor region 9 in a known manner. The measuring element 2 is advantageously produced from titanium.

The free lumen of the pipe extension piece 6 can have a cylindrical measuring electronics unit 17 inserted into it from which ribbon cables 22 can be routed to the outside via cross holes 18 in the sensor region 9 and are connected to connection points on the measuring points 11, 12.

The measuring element 2 has the free end 7 of its pipe extension piece 6 inserted into the free lumen of the pipe 4 and cemented to the inner pipe wall 8 of the latter. That end 19 of the pipe 4 which faces the adaptor connection 3 overtops the sensor region 9 and forms a spacing from the adaptor connection 3, wherein the end 19 of the pipe 4 is sealed from the adaptor connection 3 by an elastic seal 20. Hence, the pipe 4 is connected to the measuring element 2 in terms of force only by means of the free end 7 of the pipe extension piece 6. The spacing which exists between the front side 21 of the end 19 and the adaptor connection 3 and between its internal diameter or its inner pipe wall 8 and the sensor region 9 decouples the pipe end 19 in terms of force from the adaptor connection 3 and from the sensor region 9.

According to another embodiment of the invention, the pipe extension piece 6' of the measuring element 2' is integrally formed on that end 19' of the pipe 4' which faces the adaptor connection 3'. In this case, the sensor region 9' is covered by a cover 23 which is mounted on the pipe and which is decoupled in terms of force from the sensor region 9' and from the adaptor connection 3'. For the purpose of sealing, an elastic seal 20' is arranged between the cover 23 and the adaptor connection 3' in this case.

In a manner which is known per se, the alignment adaptor 5 has the shape of an inverted pyramid frustum 24 with four obliquely running planar alignment faces 25 which interact with the alignment screws 13, wherein the pyramid frustum 24 merges into a sphere-section-shaped base 26 which corresponds with a corresponding annular contact base 27 of the adaptor connection 3.

The invention claimed is:

1. A sensor device for measuring an axial force in the longitudinal pipe direction of a pipe and at least one torque, comprising:
   a measuring element having an adaptor connection;
   a pipe extension piece configured to connect the adaptor connection to the pipe, the pipe extension piece being insertable into the pipe;
   an alignment adaptor coupled to the pipe with the pipe extension;
   a plurality of strain gauges arranged at DMS measuring points in a sensor region between the adaptor connection and an end of the pipe extension piece, which is remote from the adaptor connection;
   wherein the axial force and the torque are introduced into the alignment adaptor with the measuring element and are measured with the plurality of strain gauges;
   wherein the pipe extension piece with the sensor region has a tubular design, the sensor region extends from the adaptor connection to the end of the pipe extension piece and has a smaller external diameter than the end of the pipe extension piece, an end of the pipe faces the adaptor connection and overtops the end of the pipe extension piece toward the adaptor connection and is decoupled in terms of force from the sensor region and from the adaptor connection;
   wherein the DMS measuring points include eight DMS measuring points arranged on the perimeter of the sensor region in a radial plane with a respective 22.5° offset from four alignment screws having a 90° offset.

2. The sensor device as claimed in claim 1, wherein the pipe is sealed from the adaptor connection by an elastic seal.

3. The sensor device as claimed in claim 1, wherein the alignment adaptor and the adaptor connection interact with one another via at least three alignment screws, and the number of measuring points corresponds at least to the number of alignment screws.

4. The sensor device as claimed in claim 1, wherein the alignment adaptor is in the form of an inverted pyramid frustum and has four obliquely running planar alignment faces which can interact with four alignment screws arranged in the adaptor connection, wherein the pyramid frustum merges into a sphere-section-shaped base which can correspond with a corresponding annular contact face of the adaptor connection.

5. The sensor device as claimed in claim 1, wherein additional DMS measuring points are arranged on the perimeter of the sensor region for the purpose of separate ascertainment of the axial force.

6. The sensor device as claimed in claim 5, wherein four additional DMS measuring points are arranged in a radial plane in association with the alignment screws.

7. The sensor device as claimed in one of claims claim 1, wherein each DMS measuring point has at least one strain gauge associated with a respective bridge circuit.

8. The sensor device as claimed in claim 7, wherein each measuring point has two strain gauges which are arranged next to one another in the longitudinal pipe direction with a measuring grid orientation having a 90° offset from one another.

9. The sensor device as claimed in claim 1, wherein the adaptor connection is produced from titanium in one piece with the pipe extension piece.

10. The sensor device as claimed in claim 1, wherein the sensor device is used in an artificial limb.

11. The sensor device as claimed in claim 10, wherein the sensor device is used in a leg.

12. The sensor as claimed in claim 1, wherein the sensor device is used in a robot arm of a handling apparatus.

13. The sensor device as claimed in claim 1, wherein the axial force and the at least one torque are measured with separate ones of the plurality of strain gauges.

14. A sensor device for measuring an axial force in the longitudinal pipe direction of a pipe and at least one torque, comprising:
   a measuring element having an adaptor connection;
   a pipe extension piece configured to connect the adaptor connection to the pipe, the pipe extension piece being insertable into the pipe;
   an alignment adaptor coupled to the pipe with the pipe extension;
   a plurality of strain gauges arranged at DMS measuring points in a sensor region between the adaptor connection and an end of the pipe extension piece, which is remote from the adaptor connection;
   a cover mounted on the pipe, decoupled in terms of force from the sensor region and from the adaptor connection, and arranged covering the sensor region;
   wherein the axial force and the torque are introduced into the alignment adaptor with the measuring element and are measured with the plurality of strain gauges;
   wherein the sensor region has a tubular design with a smaller external diameter than the end of the pipe extension piece the pipe extension piece is integrally molded on an end of the pipe which faces the adaptor connection,
   wherein the DMS measuring points include eight DMS measuring points arranged on the perimeter of the sensor region in a radial plane with a respective 22.5° offset from four alignment screws having a 90° offset.

15. The sensor device as claimed in claim 14, wherein the pipe or the cover is sealed from the adaptor connection by an elastic seal.

16. The sensor device as claimed in claim 14, wherein the axial force and the at least one torque are measured with separate ones of the plurality of strain gauges.

17. A sensor device for measuring an axial force in the longitudinal pipe direction of a pipe and at least one torque, comprising:
   a measuring element having an adaptor connection;
   a pipe extension piece insertable into the pipe and configured to connect the adaptor connection to the pipe, the pipe extension piece having a tubular design;
   an alignment adaptor coupled to the pipe with the pipe extension;
   a sensor region arranged between the adaptor connection and an end of the pipe extension piece, the sensor region having a smaller external diameter than the end of the pipe extension piece, the sensor region being remote from the adaptor connection and having a plurality of DMS measuring points arranged on the perimeter of the sensor region;

a plurality of strain gauges arranged at the DMS measuring points;

wherein the axial force and the torque are introduced into the alignment adaptor with the measuring element and are measured with the plurality of strain gauges, and an end of the pipe faces the adaptor connection and overtops the end of the pipe extension piece toward the adaptor connection, the pipe being decoupled in terms of force from the sensor region and from the adaptor connection.

18. The sensor device as claimed in claim 17, wherein the alignment adaptor and the adaptor connection interact with one another via at least three alignment screws, and the number of measuring points corresponds at least to the number of alignment screws.

19. The sensor device as claimed in claim 18, wherein four additional DMS measuring points are arranged in a radial plane in association with the alignment screws.

20. The sensor device as claimed in claim 17, wherein the alignment adaptor is in the form of an inverted pyramid frustum and has four obliquely running planar alignment faces which can interact with four alignment screws arranged in the adaptor connection, wherein the pyramid frustum merges into a sphere-section-shaped base which can correspond with a corresponding annular contact face of the adaptor connection.

21. The sensor device as claimed in claim 17, wherein additional DMS measuring points are arranged on the perimeter of the sensor region for the purpose of separate ascertainment of the axial force.

22. The sensor device as claimed in claim 17, wherein the plurality of DMS measuring points are arranged on the perimeter of the sensor region with a 22.5° offset from four alignment screws, which have a 90° offset.

23. The sensor device as claimed in claim 17, wherein the axial force and the at least one torque are measured with separate ones of the plurality of strain gauges.

24. The sensor device as claimed in claim 17, wherein the axial force is measured by a first half of the plurality of strain gauges, and the at least one torque is measured by a second half of the plurality of strain gauges.

* * * * *